US012222350B1

(12) United States Patent
Mohanty et al.

(10) Patent No.: US 12,222,350 B1
(45) Date of Patent: Feb. 11, 2025

(54) DIFFERENTIAL SENSOR MEASUREMENT METHODS AND STRUCTURES

(71) Applicant: FemtoDx, Inc., Beverly Hills, CA (US)

(72) Inventors: Pritiraj Mohanty, Beverly Hills, CA (US); Shyamsunder Erramilli, Quincy, MA (US)

(73) Assignee: FemtoDx, Inc., Beverly Hills, CA (US)

( * ) Notice: Subject to any disclaimer, the term of this patent is extended or adjusted under 35 U.S.C. 154(b) by 0 days.

(21) Appl. No.: 15/242,755

(22) Filed: Aug. 22, 2016

Related U.S. Application Data

(63) Continuation of application No. 14/510,178, filed on Oct. 9, 2014, now abandoned.
(Continued)

(51) Int. Cl.
*G01N 33/543* (2006.01)
*C12Q 1/00* (2006.01)
(Continued)

(52) U.S. Cl.
CPC ......... *G01N 33/5438* (2013.01); *C12Q 1/001* (2013.01); *H01L 29/0649* (2013.01);
(Continued)

(58) Field of Classification Search
CPC ................ G01N 33/5438; C12Q 1/001; H01L 29/0649; H01L 29/0669; H01L 29/16; H01L 29/78
See application file for complete search history.

(56) References Cited

U.S. PATENT DOCUMENTS

| 4,728,882 A | 3/1988 | Standbro et al. |
| 2006/0188934 A1* | 8/2006 | Chang .................. B81B 3/0032 435/7.1 |

(Continued)

FOREIGN PATENT DOCUMENTS

| WO | WO 2008/063901 A1 | 5/2008 |
| WO | WO 2009/124111 A2 | 10/2009 |
| WO | WO 2016/089453 A1 | 6/2016 |

OTHER PUBLICATIONS

Akiyama, T., Nicolas Blanc, and Nics F. de Rooij. "A force sensor using a CMOS inverter in view of its application in scanning force microscopy."Micro Electro Mechanical Systems, 1996, MEMS'96, Proceedings. An Investigation of Micro Structures, Sensors, Actuators, Machines and Systems. IEEE, The Ninth Annual International Workshop on. IEEE, 1996.*
(Continued)

*Primary Examiner* — Robert J Eom
(74) *Attorney, Agent, or Firm* — Wolf, Greenfield & Sacks, P.C.

(57) ABSTRACT

Systems and methods for detection of biological agents are generally described. Certain embodiments relate to circuits comprising a first semiconductor nanosensor and a second semiconductor nanosensor in electrical communication with the first semiconductor nanosensor. The circuit can be configured to output a differential electrical property between the first semiconductor nanosensor and the second semiconductor nanosensor when exposed to a sample comprising an analyte. In certain instances, the first semiconductor nanosensor is functionalized with a detector species, and the second semiconductor nanosensor is not functionalized with the detector species. In some cases, the first semiconductor nanosensor is functionalized with a detector species, and the second semiconductor nanosensor is associated with a gate.

15 Claims, 7 Drawing Sheets

Related U.S. Application Data (60) Provisional application No. 61/888,830, filed on Oct. 9, 2013.

(51) Int. Cl.
 H01L 29/06 (2006.01)
 H01L 29/16 (2006.01)
 H01L 29/78 (2006.01)

(52) U.S. Cl.
 CPC .......... *H01L 29/0669* (2013.01); *H01L 29/16* (2013.01); *H01L 29/78* (2013.01)

(56) References Cited

U.S. PATENT DOCUMENTS

| | | |
|---|---|---|
| 2006/0208254 A1 | 9/2006 | Goodman et al. |
| 2009/0309614 A1 | 12/2009 | Goodman et al. |
| 2010/0033058 A1 | 2/2010 | Lee et al. |
| 2010/0039126 A1 | 2/2010 | Chen et al. |
| 2011/0021894 A1 | 1/2011 | Mohanty et al. |
| 2012/0040844 A1* | 2/2012 | Rothberg ......... G01N 33/54373 506/7 |
| 2019/0094174 A1 | 3/2019 | Mohanty et al. |
| 2020/0088723 A1 | 3/2020 | Mohanty et al. |

OTHER PUBLICATIONS

Sparreboom, Wouter, Albert van den Berg, and Jan CT Eijkel. "Principles and applications of nanofluidic transport." Nature nanotechnology 4.11 (2009): 713. (Year: 2009).*

Gao, Anran, et al. "Silicon-nanowire-based CMOS-compatible field-effect transistor nanosensors for ultrasensitive electrical detection of nucleic acids." Nano letters 11.9 (2011): 3974-3978. (Year: 2011).*

De, Arpita, et al. "Integrated label-free silicon nanowire sensor arrays for (bio) chemical analysis." Analyst 138.11 (2013): 3221-3229. (Year: 2013).*

International Search Report and Written Opinion for PCT/US2019/064678 mailed Feb. 6, 2020.

Maedler et al., Tunable Nanowire Wheatstone bridge for improved sensitivity in molecular recognition. Applied Physics Letters. 2013;102:043112. 4 pages.

* cited by examiner

DIFFERENTIAL SENSOR MEASUREMENT METHODS AND STRUCTURES

RELATED APPLICATIONS

This application is a continuation of U.S. patent application Ser. No. 14/510,178, filed Oct. 9, 2014, which claims priority under 35 U.S.C. § 119(e) to U.S. Provisional Patent Application Ser. No. 61/888,830, filed Oct. 9, 2013, which are incorporated herein by reference in their entirety for all purposes.

TECHNICAL FIELD

Systems and methods for detection of biological agents are generally described.

BACKGROUND

Biosensors generally comprise devices integrated with a biological sensing element (also referred to herein as a detector species) and a signal transducer, which can provide a recognition signal of the presence of a specific substance. The biological sensing element is often a product derived from a living system. For example, the biological sensing element may comprise, for example, an enzyme, an antibody, and/or a nucleic acid. The biological sensing element (and/or another analyte-detecting molecule) generally determines the specificity of the biosensor. The specific binding or reaction between the target and the receptor (or the biological sensing element) can introduce a signal that is then transduced and measured. Biosensors can be configured for macromolecular recognition, such as with human cells of different types, viruses, and pathogenic organisms. Therefore, there is a far-reaching diagnostic utility in these devices ranging from applications towards human health, food safety, drug response, and personalized medicine.

Biosensors may be categorized by their operational mechanism. Although optical biosensors using colorimetric, fluorescence, luminescence, and absorbance are industry and diagnostics standards, these strategies often necessitate target labeling and amplification. Also, the instrumentation footprint necessary to sensitively read optically-based signals is large compared with that achievable with devices incorporating nanotechnologies and microelectronics. Thus, technologies that improve the sensitivity, cost, instrumentation, and/or field applicability of biosensors are desirable.

SUMMARY

Systems and methods for the detection of biological agents are provided. Certain of the sensors described herein may be used to sense chemical or biological species (also referred to as analytes), for example in an analyte solution (e.g., a sample). Certain embodiments are related to nanoscale sensors (i.e., nanosensors), such as sensors implemented using semiconductor devices, or similar small-scale electrical devices, as sensitive transducers to convert chemical activity of interest into corresponding electrical signals representative of the chemical activity.

The subject matter of the present invention involves, in some cases, interrelated products, alternative solutions to a particular problem, and/or a plurality of different uses of one or more systems and/or articles.

According to certain embodiments, a circuit is provided. The circuit comprises, in some embodiments, a first semiconductor nanosensor functionalized with a detector species; and a second semiconductor nanosensor that is not functionalized with the detector species and is in electrical communication with the first semiconductor nanosensor; wherein the circuit is configured to output a differential electrical property between the first semiconductor nanosensor and the second semiconductor nanosensor when exposed to a sample comprising an analyte.

In certain embodiments, the circuit comprises a first semiconductor nanosensor functionalized with a detector species; and a second semiconductor nanosensor associated with a gate and in electrical communication with the first semiconductor nanosensor; wherein the circuit is configured to output a differential electrical property between the first semiconductor nanosensor and the second semiconductor nanosensor when exposed to a sample comprising an analyte, and wherein the circuit is configured to detect a lower concentration of the analyte than an identical circuit lacking the gate.

In some embodiments, the first and second semiconductor nanosensors are positioned such that the smallest distance between the first and second semiconductor nanosensors is less than or equal to about 1 mm.

Some embodiments comprise a phase shifter in electrical communication with the first semiconductor nanosensor, the second semiconductor nanosensor, and a voltage source. In some embodiments, the phase shifter is configured to produce a first signal and a second signal having a phase that is shifted in phase by 180° relative to the first signal.

Certain embodiments comprise a gate associated with the second semiconductor nanosensor. In some embodiments, the gate is configured to modulate a signal from the first and/or second semiconductor nanosensor. In certain embodiments, the gate is positioned over the second semiconductor nanosensor. In some embodiments, the gate is positioned to the side of the second semiconductor nanosensor. According to certain embodiments, the gate is configured to receive a voltage and alter at least one electrical property of the second semiconductor nanosensor.

In some embodiments, the differential electrical property is a differential voltage. In certain embodiments, the differential electrical property is a differential current. According to some embodiments, the differential electrical property is a differential conductance. The differential electrical property can be, in some embodiments, a differential resistance.

Certain embodiments comprise a third semiconductor nanosensor in electrical communication with the first and second semiconductor nanosensors; and a fourth semiconductor nanosensor in electrical communication with the first, second, and third semiconductor nanosensors.

In some embodiments, at least one of the semiconductor nanosensors comprises a plurality of nanostructures formed in the semiconductor nanosensor. The nanostructures are, in some embodiments, nanochannels. In some embodiments, at least one nanostructure has a cross-sectional dimension of less than or equal to about 150 nm.

In certain embodiments, at least one of the semiconductor nanosensors comprises a field effect transistor.

According to certain embodiments, the semiconductor comprises silicon.

In some embodiments, the analyte is a protein, a nucleic acid, a monosaccharide, and/or a polysaccharide. In some embodiments, the detector species is an enzyme, an antibody, and/or a nucleic acid.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Systems and methods for the detection of biological agents are generally described. Certain embodiments relate to a circuit, which can be used as part of a biosensor.

For many sensing applications, it is beneficial to employ sensors having high sensitivity to an analyte of interest. Sensors with high sensitivity can be used to detect much smaller amounts or concentrations of the analyte, which may be desirable (or, in certain instances, necessary) in some applications. In addition, such sensors can, in certain cases, provide a high signal-to-noise ratio, and thus improve the quality of measurements that are taken using such sensors.

Producing sensitive biosensors that selectively detect target analytes and/or molecular binding events can be challenging, however. For example, oftentimes, a primary binding event of low abundance proteins may be masked by less specific interactions of many other proteins, or proteins of high abundance. Proper execution of the device should yield adequate sensitivity and specificity information in order to address adequately the field application needs in medical diagnostics, public health, epidemiologic studies, personalized medicine, monitoring/surveillance, agriculture, and defense industries.

Thus, certain aspects relate to configurations in which the sensitivity of the circuit to the detection of a target analyte is enhanced.

Certain embodiments relate to devices and methods using a sensing device comprising two or more nanosensors. The nanosensors can correspond to nanochannels, which can be constructed, in certain embodiments, from a semiconductor material. In some embodiments, the nanosensors are connected, at opposing ends, to electrodes. In certain embodiments, at least one of the nanosensors is treated (e.g., functionalized) with a detection species, which associates with (e.g., functionalizes) surfaces of at least one of the nanosensors such that the surfaces associated with the detector species are configured to interact with at least one analyte. In some such embodiments, one or more of the nanosensors have at least one electrical property that varies based, at least in part, on an interaction between a detector species associated with the nanosensor surface and at least one analyte (also referred to as "agent") contained in a sample (also referred to as an "analyte solution") introduced to the sensor. In certain embodiments, the sensing device includes a controller to control sensitivity of the sensor to the presence of the at least one analyte. In some embodiments, the controller configured to control the sensitivity of the one or more nanosensors is configured to cause voltage to be applied to at least one of the one or more nanosensors to cause conductance of the at least one of the one or more nanosensors to change (optionally, in a controlled manner). In some embodiments, the sensing circuit comprises a gate structure of a field effect transistor (FET), and the electrodes connected to the nanosensors can correspond to the source and drain of the FET.

The systems described herein can be configured to detect any suitable type of analyte. For example, in some embodiments, the system is configured to detect a protein, a nucleic acid, a monosaccharide, and/or a polysaccharide.

In some embodiments, the circuit comprises a first semiconductor nanosensor and a second semiconductor nanosensor in electrical communication with the first semiconductor nanosensor. The first and second semiconductor nanosensors can be configured, according to certain embodiments, such that the circuit exhibits a sensitivity that is greater than a sensitivity that would be exhibited by an equivalent circuit including only one of the nanosensors.

In some embodiments, the first semiconductor nanosensor can be functionalized with a detector species, and the second semiconductor nanosensor can be configured such that it is not functionalized with the detector species. In some such embodiments, the circuit can be configured to output a differential electrical property between the first semiconductor nanosensor and the second semiconductor nanosensor when exposed to a sample comprising an analyte. In this way, the second semiconductor nanosensor can provide a baseline measurement that is filtered out of the signal produced by the first semiconductor nanosensor, allowing for more sensitive detection of the analyte.

In certain embodiments, a gate can be associated with the second semiconductor nanosensor. The gate can be used to modify an electrical property (e.g., resistance) of the second semiconductor nanosensor, which can improve the sensitivity of the sensing circuit. In some embodiments, the nanosensor(s) can be part of a bias and measurement circuit.

As noted above, the sensing circuit comprises a nanosensor, in certain embodiments. Those of ordinary skill in the art are familiar with nanosensors, which are sensing elements including at least one nanoscale dimension. In some embodiments, the nanosensor is elongated. The nanosensor may have a cross-sectional dimension, in some embodiments, of less than 500 nm, less than 100 nm, or less than 50 nm (and/or, in some embodiments, as little as 1 nm, or smaller). In some embodiments, the nanosensor comprises a nanochannel. The sensing circuits described herein can include one, two, three, four, or more nanosensors (e.g., nanochannels). In one exemplary embodiment, each nanochannel has a cross section of about 100 nm by 150 nm or smaller.

The nanosensors described herein can be biosensors, in some embodiments. The nanosensors can be configured to detecting an analyte, which can be a chemical or biological species. In some embodiments, one or more of the nanosensors comprises an outer surface that is functionalized with a detector species. In certain embodiments, the detector species can chemically interact (directly or indirectly) with the analyte of interest. In some embodiments, the interaction between the detector species and the analyte of interest creates a corresponding change in surface potential. In some embodiments, the nanosensor has a sufficiently small cross section to exhibit a shift of an electrical characteristic (e.g., a differential conductance characteristic). The shift of the electrical characteristic can be a shift into a negative bias operating region. The amount of the shift can be dependent on the surface potential or the surface charge. Functionalization of nanosensors can be performed according to standard protocols. For example, in certain embodiments in which urea is being sensed, the nanosensor(s) can be functionalized with urease. In certain embodiments in which glucose is being sensed, the nanosensor(s) can be functionalized with glucose oxidase. In some embodiments in which antigens are being sensed, the nanosensor(s) can be functionalized with one or more antibodies.

In some embodiments, a nanosensor within the circuit is made of a semiconductor material. Suitable semiconductor materials from which a nanosensor can be made include, but are not limited to, silicon, germanium, III-V semiconductors, and the like. In some embodiments, the nanosensor is made of silicon.

The sensing circuit may employ, in some embodiments, a field-effect nanosensor. Generally, field effect transistors (FETs) use an electric field to control the electrical channel of conduction, and hence the conductivity of the charge carriers in the channel. The flow of charge carriers between the source and the drain can be tuned by modifying the size and the shape of the conducting channel by applying an electric field to the gate. In an exemplary biosensor configuration, the FET comprises a nanosensor (e.g., nanowire) channel between source and drain terminals. The nanosensor (e.g., nanowire) surface can be bio-functionalized so that a biomolecular binding event can create an electric field, similar to the control electric field applied to a conventional FET as shown in FIGS. 1A-1E. In certain devices that use the FET, a designated, physically separated sensor surface can be formed by precision manufacturing. The FET sensor can be connected to an electronic circuit to monitor the specific conductance of the sensor surface. In some embodiments, operationally, many independent electronic circuits may be interrogated in a massively parallel manner. FET biosensors can be adapted for the measurement of biomolecules interacting with such a sensor surface as shown in FIGS. 1A-1E. The surface of a FET biosensor can be modified to selectively recognize one or more specific analytes. In some embodiments, species (e.g., antibodies) can be conjugated to the nanosensor surface as part of the manufacturing process. These species (e.g., antibodies) can be selected for specific detection of an analyte (e.g., a protein) of interest. Molecular binding events between the analyte and the species (e.g., antibodies) on the biosensor surface can cause changes to the biosensor surface charge density and/or surface potential. In this manner, precision manufacturing of FET biosensors can allow for sensitive analyte recognition. The differential conductance amplitude can be correlated to the analyte concentration in the sample solution.

Figure 1A:
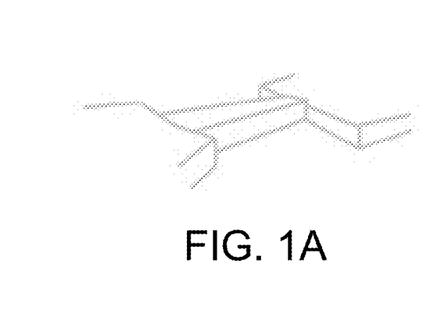
FIG. 1A is a schematic illustration of an exemplary nanosensor, according to certain embodiments.
Figure 1B:
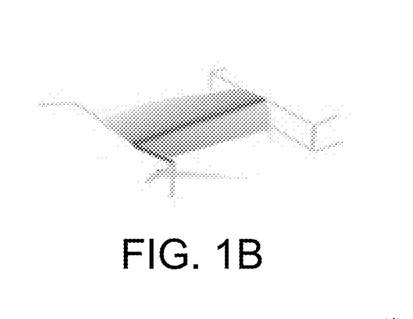
FIG. 1B is a schematic illustration of an exemplary nanosensor, according to certain embodiments.
Figure 1C:
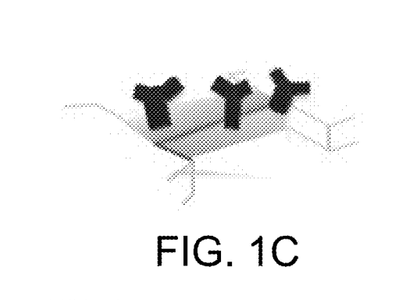
FIG. 1C is a schematic illustration of an exemplary nanosensor, according to certain embodiments.
Figure 1D:
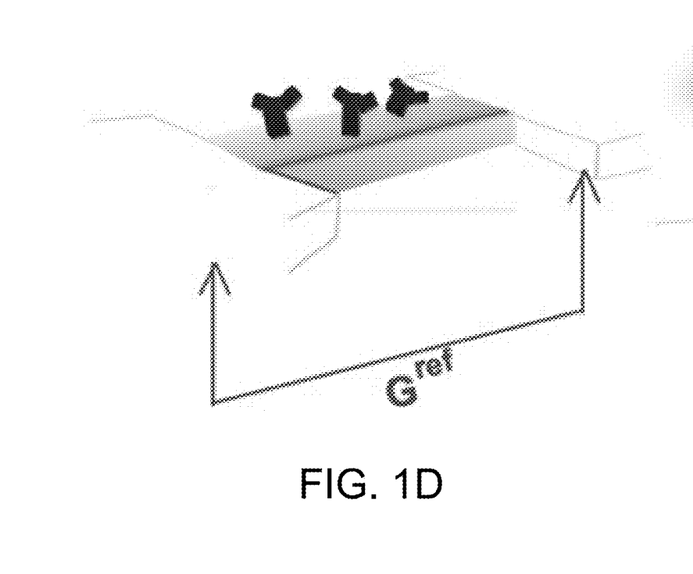
FIG. 1D is a schematic illustration of an exemplary nanosensor, according to certain embodiments.
Figure 1E:
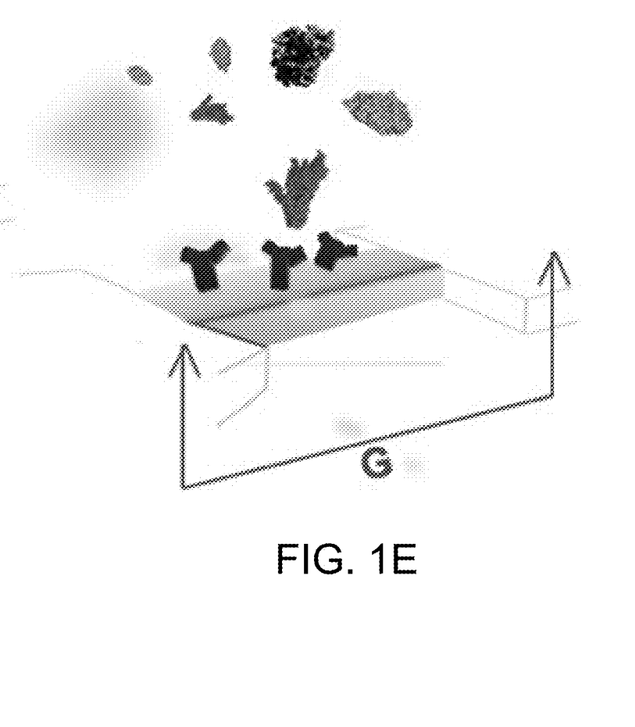
FIG. 1E is a schematic illustration of an exemplary nanosensor, according to certain embodiments.

In one particular set of embodiments, stepwise manufacturing of FET devices for diagnostic tests can be employed as illustrated in FIGS. 1A-1E. Nanosensors of precise dimensionality and surface area can be formed that are highly sensitive to surface charge changes. Following a process of lithography (FIG. 1A) and chemistry (FIG. 1B, shaded area), antibodies can be conjugated to the surface of the sensor (FIG. 1C). Analyte measurements as illustrated in FIGS. 1D-1E can be conducted with samples containing heterogeneous mixtures of disease-relevant proteins, such as occurs in blood, saliva, and other fluids. Specific analyte binding can contribute to a surface charge differential, detected electrically as a change in conductance (delta G, ΔG) across the nanosensor surface. In FIGS. 1B-1E, areas that are not shaded are a source and a drain for every nanosensor.

In some embodiments, lithographic methods are used to fabricate gates at the bottom, the top, and/or the side of the nanosensors. In some embodiments, the nanochannels' surfaces can be functionalized with a specific receptor or antibody to interact with agents/species of interest. In a fluid, the ligand (or antigen) can bind to the receptor, which can result in a change in the surface charge profile and the surface potential. This binding can behave as a field effect. The conductance and the I-V characteristics of the nanochannel can therefore be used to characterize biomolecular binding. For example, the conductance and/or the I-V characteristics of the nanochannel can be used, in some embodiments, to determine concentration and/or binding dissociation constants. In some embodiments, characteristics of the derivative of current with respect to voltage (dI/dV) can be used for even higher sensitivity in the field effect transistor due to biomolecular binding. In some such embodiments, dI/dV characteristics allow measurement at low bias. The use of low bias can be helpful in avoiding electrolysis.

In some embodiments, the nanosensor(s) can be part of a bias and measurement circuit. In some embodiments, the bias and measurement circuits are operated by applying a bias voltage across two ends of nanosensors (e.g., nanochannels) within the circuit. The bias voltage can be selected to be sufficiently negative to achieve a desired dependence of dI/dV of the sensing element on the surface potential of the nanochannels. In certain embodiments, this dependence has a steeply sloped region of high amplification which is substantially greater than a reference amplification exhibited by the sensing element at a zero-bias condition, thus achieving relatively high signal-to-noise ratio. The bias and measurement circuit measures, in some embodiments, the derivative of current with respect to voltage (dI/dV) of the sensing element and converts the measured dI/dV into a signal indicative of presence or activity of the analyte. In certain embodiments, the measured dI/dV can be converted into a signal indicative of the presence or activity of the analyte by using a look-up table or alternative conversion mechanism reflecting a prior calibration operation. In some embodiments, applied gate voltage can be used to control a sensor's sensitivity. The bias and reference gate voltage can be used independently, according to certain embodiments, to control sensitivity.

Certain embodiments relate to the use of differential measurements to improve sensitivity of the sensing circuits described herein. One of the major challenges in nanoelectronic detection of biological or chemical species is low signal to noise ratio. Low signal to noise ratios may be the result of large background noise (e.g., a large amount of noise in the baseline signal). Moreover, in many cases, due to the dynamic changes in presence of a fluid sample, both short-term and long-term stabilities in the background can become difficult to achieve. Such issues may result in a relatively low sensitivity (signal-to-noise ratio) of the sensing device.

One approach that can be used to address the dynamic background changes is to use a difference measurement technique. In one set of embodiments, two sensors are employed for detection. In some such embodiments, a first nanosensor is functionalized with a detector species, and a second nanosensor is not functionalized with the detector species and is in electrical communication with the first semiconductor nanosensor. In some such embodiments, the first and second semiconductor nanosensors are positioned such that the smallest distance between the first and second semiconductor nanosensors is less than or equal to about 1 mm. In certain such embodiments, because the nanosensors are relatively closely spaced, they experience almost the same environmental conditions (and changes in conditions). Therefore, in some such embodiments, a difference in an electrical property (e.g., voltage, current, conductance, and/or resistance) generated in the two sensors can be used to detect a signal where the backgrounds are subtracted out.

The circuits described herein can be configured to output a variety of differential electrical properties. For example, in some embodiments, the circuit can be configured to output a differential voltage between a first nanosensor and a second nanosensor when exposed to a sample comprising an analyte. For example, the circuit can be configured to output a signal that is indicative of the difference between the voltage across the second nanosensor and the voltage across the first nanosensor when the circuit is exposed to a sample comprising an analyte. In certain embodiments, the circuit can be configured to output a differential current between a first nanosensor and a second nanosensor (e.g., a signal indicative of the difference between the current through the first nanosensor and the current through the second nanosensor), when exposed to a sample comprising an analyte. In certain embodiments, the circuit can be configured to output a differential conductance between a first nanosensor and a second nanosensor (e.g., a signal indicative of the difference between the conductance through the first nanosensor and the conductance through the second nanosensor), when exposed to a sample comprising an analyte. In certain embodiments, the circuit can be configured to output a differential resistance between a first nanosensor and a second nanosensor (e.g., a signal indicative of the difference between the resistance through the first nanosensor and the resistance through the second nanosensor), when exposed to a sample comprising an analyte.

In some embodiments, the sensor circuit comprises two sensors connected to each other in a bridge configuration. The system may contain, in some embodiments, a phase shifter. The phase shifter can be configured, according to certain embodiments, to produce independent signals from the two sensors that are separated in phase by 180 degrees. For example, in some embodiments, an input voltage can be applied through a phase shifter that produces two signals with 0 and 180 degree phase shift with respect to the input voltage. The differential voltage between the signals from the two sensors can then be detected, in some embodiments, by an electrode coupled to both sensors. For example, in some embodiments, the output can be read from a common electrode, which produces a difference voltage. In some embodiments, one of the sensors is isolated by a layer coated on top, and the differential voltage reflects the changes due to biological binding. Moreover, in some embodiments, a top-gate voltage can be applied to the isolated sensor to tune or null the difference of the voltage in the absence of binding. Such a technique can dramatically enhance the sensitivity of the sensor.

Figure 2:
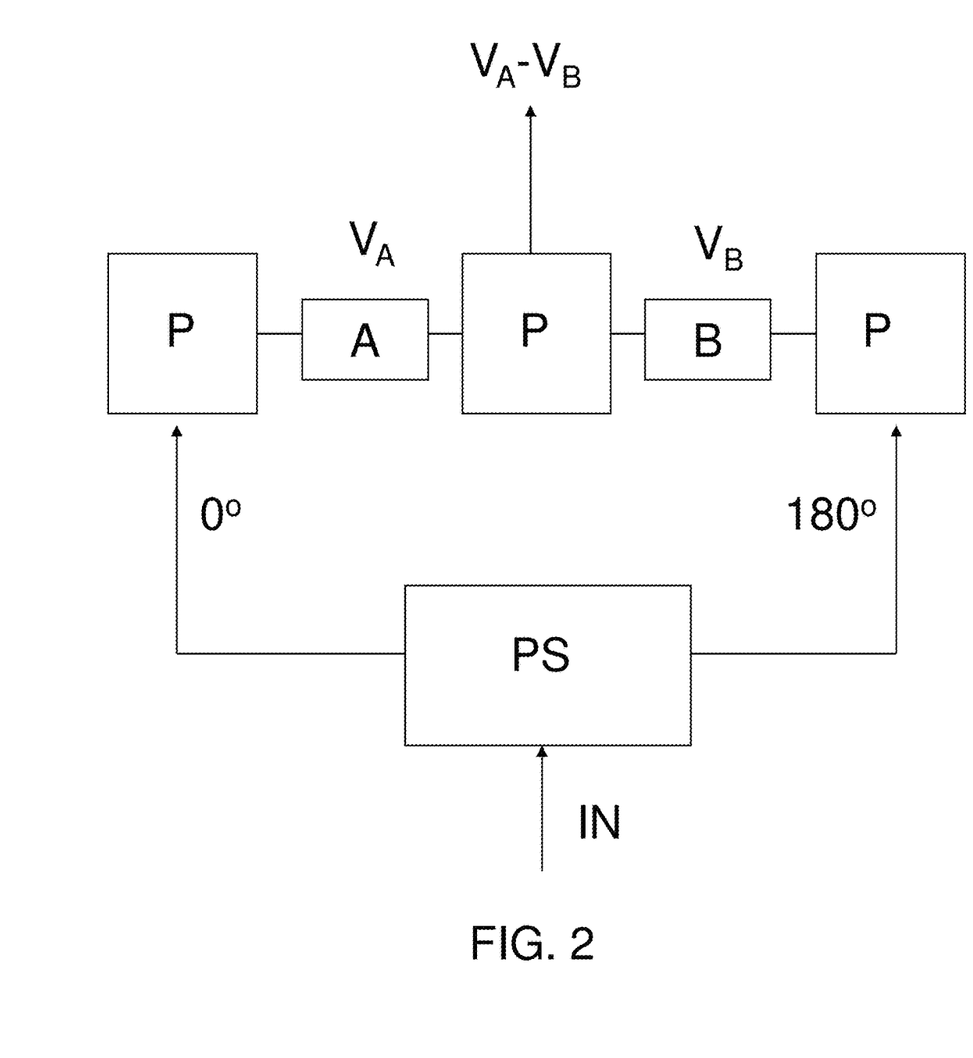
FIG. 2 is a schematic illustration of a system in which two nanosensors (A and B) are connected in a bridge configuration.

FIG. 2 is a schematic illustration of an exemplary system in which two nanosensors are employed. In FIG. 2, two nanosensors (A and B) are connected in a bridge configuration. In FIG. 2, P indicates electrode pads and PS indicates a phase shifter. The phase shifter can be used to produce signals that are shifted in phase by 180 degrees. For example, the phase shifter can be used to produce signals that are shifted by 0 and 180 degrees relative to an input signal. The voltages across the two sensors are indicated by $V_A$ and $V_B$. The difference of the two sensor voltages can be detected at a central pad (e.g., between sensors A and B in FIG. 2). An input bias can be applied across two of the pads at points indicated as IN.

Figure 4:
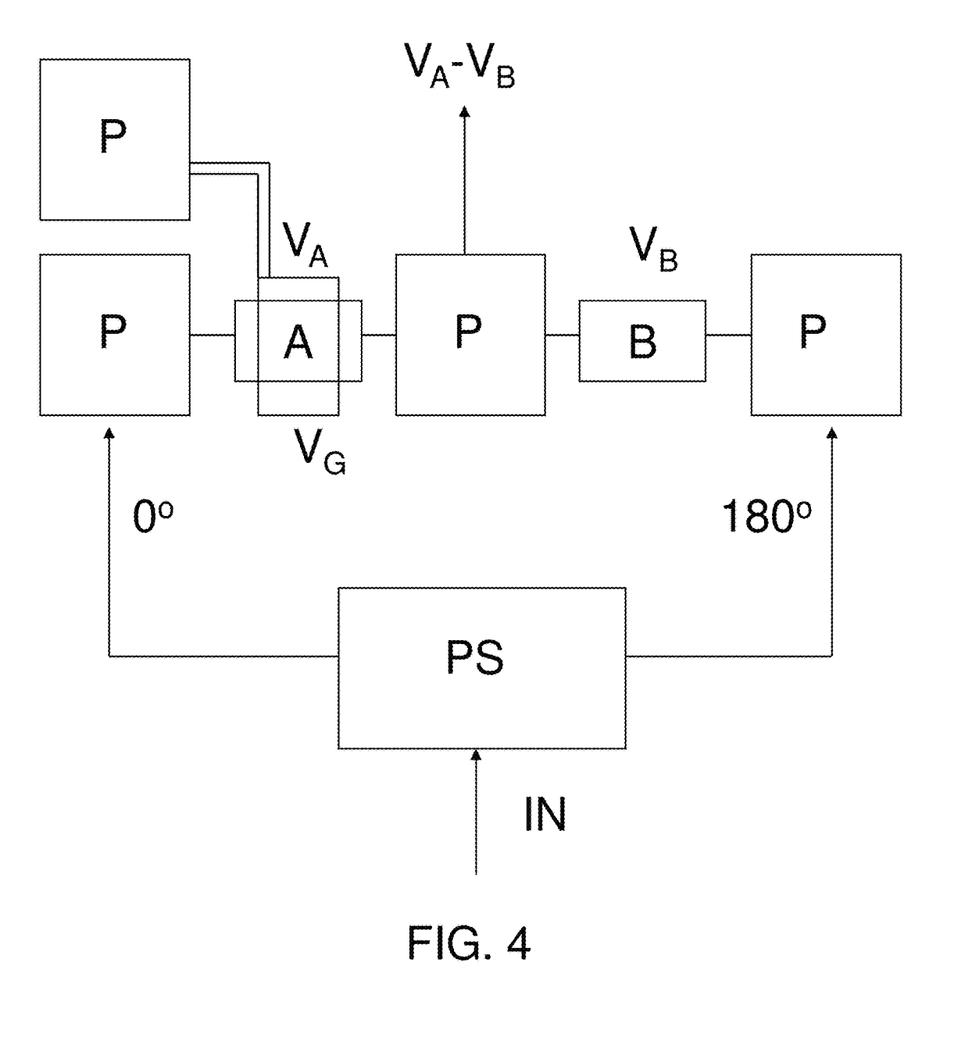
FIG. 4 is a schematic illustration of an exemplary embodiment of a two-nanosensor bridge network.

FIG. 4 is a schematic illustration of an exemplary system in which a gate is associated with one of the nanosensors in the system. In FIG. 4, nanosensors A and B are part of a two-nanosensor bridge network. The difference between the voltage across sensor A and the voltage across sensor B can be detected. An additional top gate can be added either at nanosensor A (as shown in FIG. 4) and/or nanosensor B. The gate can be used, according to certain embodiments, to tune or modulate the nanosensor with which the gate is associated. The local tuning can be used, for example, to match the resistances of the two resistors and/or to tune in a null voltage at the central connecting electrode P. An input bias can be applied across two of the pads at points indicated as IN.

In another approach, a network containing more than two sensors can be constructed. The configuration of this network can be designed to produce a net signal, such as a voltage, across two specific points of the network, which is related to a signal representing the binding of an analyte to one of the sensor surfaces. Furthermore, the topology of the network can be optimized, where an increased sensitivity of detection of analyte binding to the one nanosensor surface is resolved.

For example, in some embodiments, the sensor circuit comprises four nanosensors. In some such embodiments, at least one of the nanosensors has a surface associated (e.g., functionalized) with a detector species. The four nanosensors can be connected in a bridge configuration, in some embodiments. In some such embodiments, the bridge is designed to produce a null voltage across two points of the bridge. Standard nulling techniques can be used to cancel out the dynamic changes in the resistances. Therefore, a small change in the functionalized sensor (one of the sensors in the network) can be amplified. Performing the detection step in this manner can increase the sensitivity of the detection of an analyte binding to one of the nanosensors.

Figure 3:
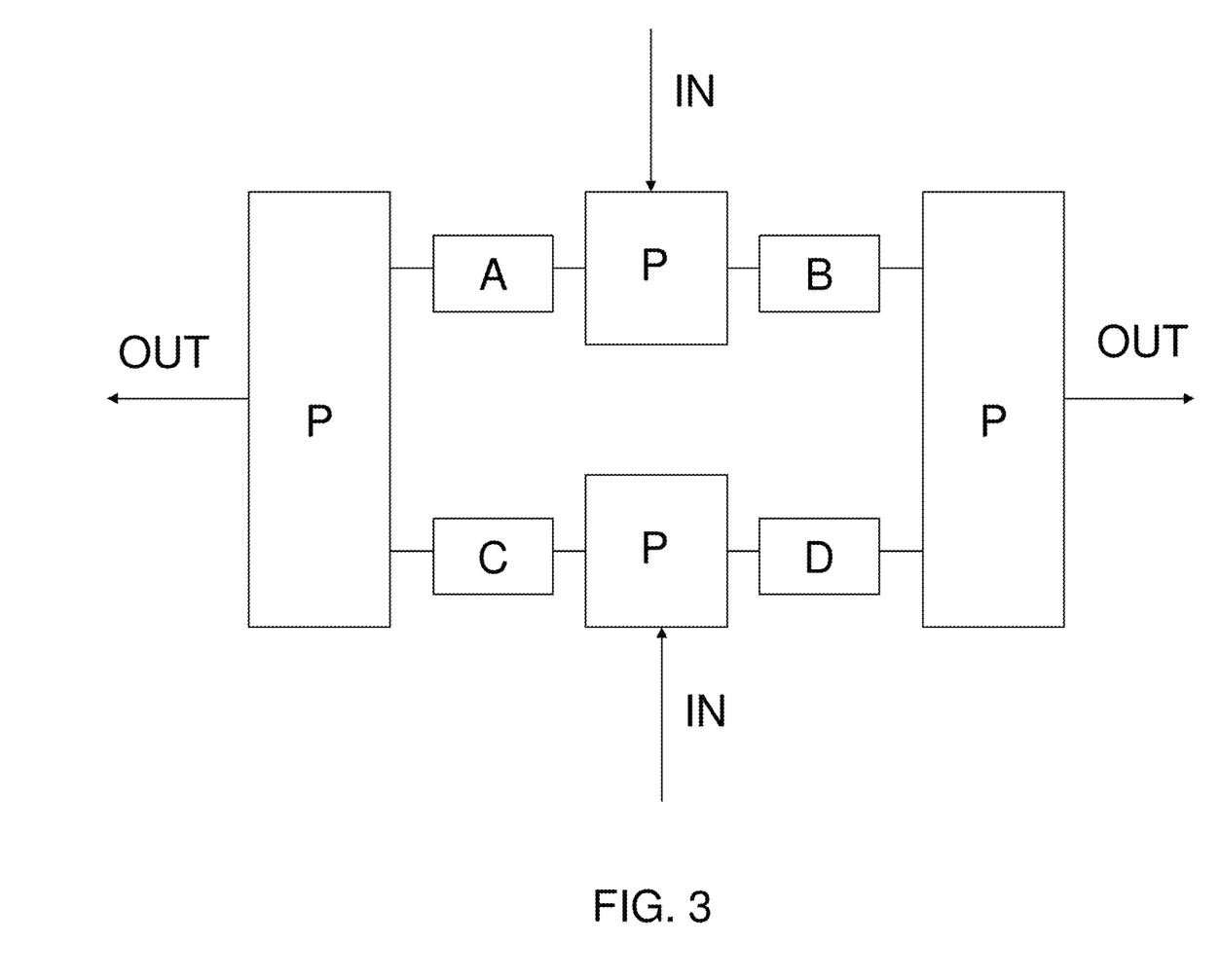
FIG. 3 is a schematic illustration of an exemplary embodiment of a Wheatstone bridge circuit block diagram for nanosensors.

FIG. 3 is a schematic illustration of an exemplary system in which four nanosensors (A, B, C, and D) are employed. FIG. 3 shows a Wheatstone bridge circuit block diagram for the four nanosensors. In FIG. 3, nanosensors A, B, C and D are connected through electrical pads P. An input bias can be applied across two of the pads at points indicated as IN. The output can be recorded across the pads indicated as OUT.

Figure 5:
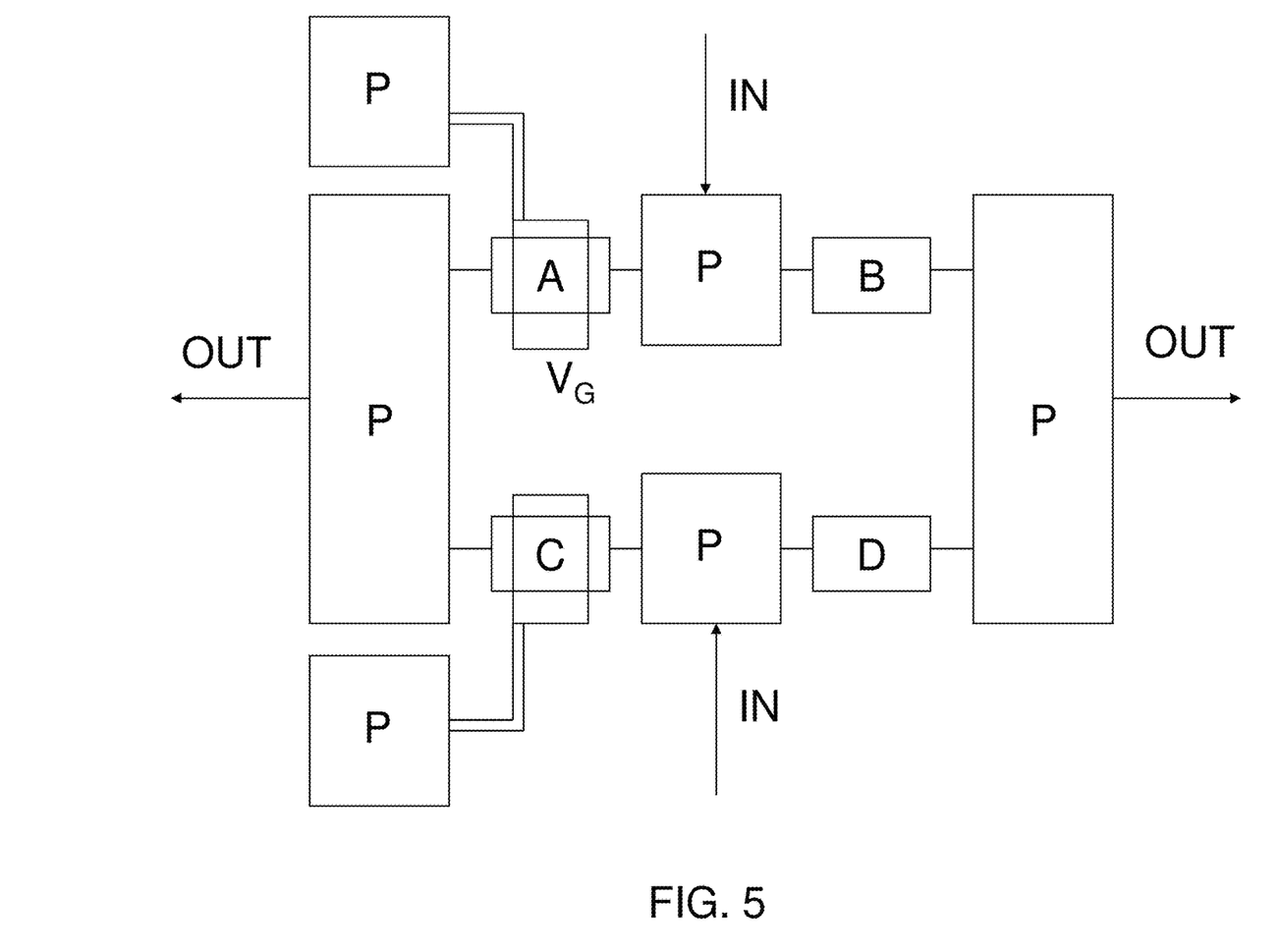
FIG. 5 is a schematic illustration of an exemplary embodiment of a Wheatstone bridge of four nanosensor network.

FIG. 5 is another schematic illustration of an exemplary system in which four nanosensors (A, B, C, and D) are employed. FIG. 5 shows a Wheatstone bridge of the 4 nanosensor network. One (or more) of the nanosensors can have a top gate for local tuning of the corresponding resistances or to create a null voltage across the OUT electrodes.

Figure 6:
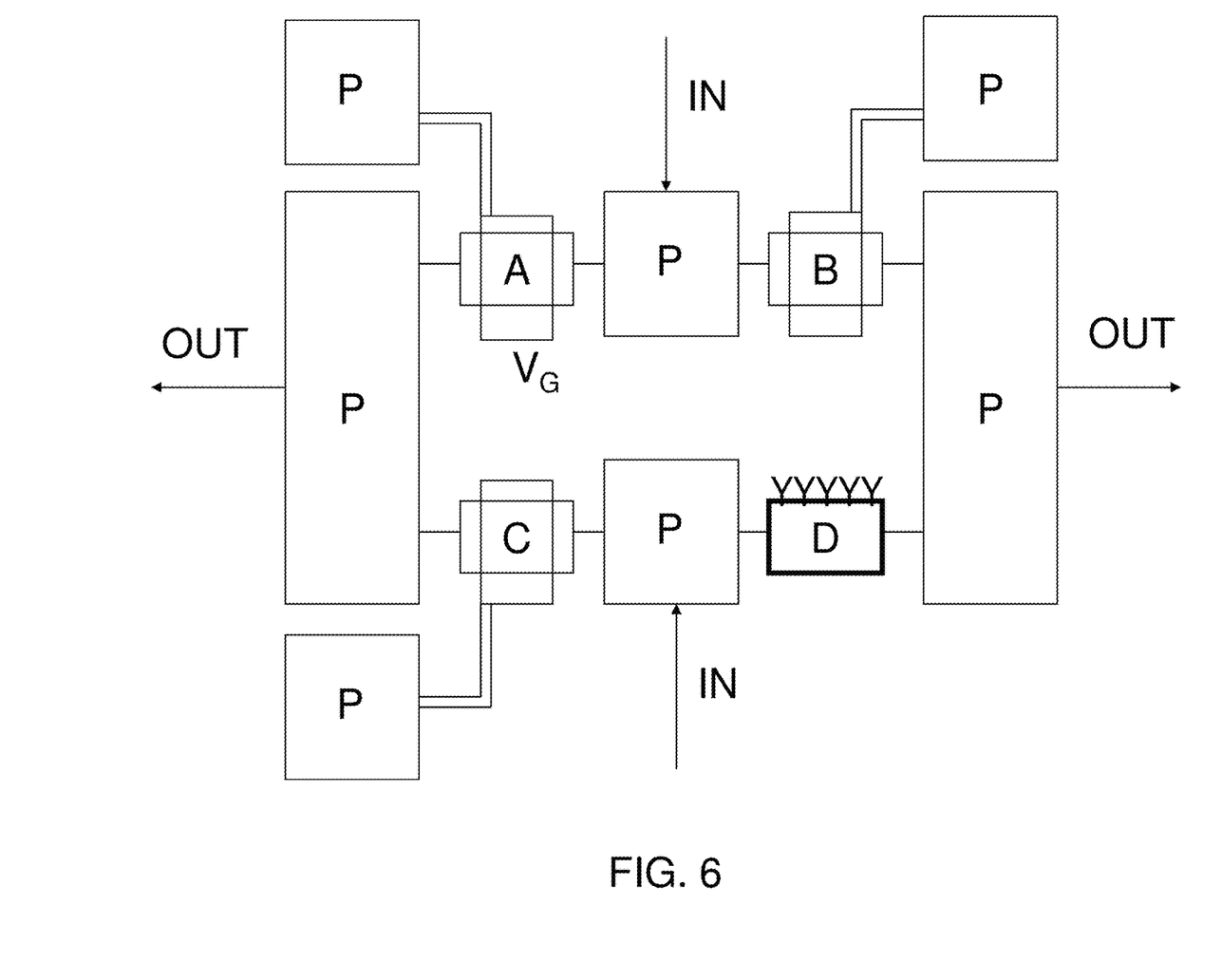
FIG. 6 is a schematic illustration of an exemplary embodiment of a four nanosensor Wheatstone bridge network.

FIG. 6 is another schematic illustration of an exemplary system in which four nanosensors (A, B, C, and D) are employed in a Wheatstone bridge network. In FIG. 6, three of the nanosensors (A, B and C) are isolated (e.g., by coating of an oxide layer) with a local gate electrode for tuning. One of the nanosensors (D in FIG. 6) is exposed and functionalized. Nanosensors A, B and C can be tuned by local gate voltages for creating a null voltage across the OUT electrodes.

An exemplary mode of operation of a four sensor network is now described. It should be understood that, while this example describes a system in which four nanosensors are employed, the system could include more than four nanosensors, in some embodiments.

A typical Wheatstone bridge circuit contains 4 resistances $R_A$, $R_B$, $R_C$ and $R_D$. In the nanosensor network, the four resistances correspond to the resistance of four nanosensors (e.g., A, B, C, and D in FIGS. 3, 5, and/or 6). For an applied voltage input $V_{IN}$, the output voltage reading will be $$V_{OUT} = \frac{R_A R_C - R_B R_D}{(R_A + R_B)(R_C + R_D)} V_{IN}.$$

This voltage can be measured, for example, while the device is not exposed to the target analyte (e.g., while the device is not exposed to the sample fluid).

If the device is exposed to the target analyte (e.g., to a fluid containing the target analyte), then all resistances will change, resulting in a changed output voltage:

$$V_{OUT} + \Delta V_{OUT} = \frac{(R_A + \Delta R_A)(R_C + \Delta R_C) - (R_B + \Delta R_B)(R_D + \Delta R_D)}{(R_A + \Delta R_A + R_B + \Delta R_B)(R_C + \Delta R_C + R_D + \Delta R_D)} V_{IN}.$$

In the balanced condition (before exposure to fluid), the output voltage is zero. The resistances must satisfy the following condition:

$$\frac{R_A}{R_B} = \frac{R_C}{R_D} = \frac{1}{r}.$$

Assuming that the resistance change is small, one can express an approximate expression for the change in the output voltage as follows:

$$\Delta V_{OUT} \approx \frac{r}{(1+r)^2} \left[ \frac{\Delta R_A}{R_A} - \frac{\Delta R_B}{R_B} + \frac{\Delta R_C}{R_C} - \frac{\Delta R_D}{R_D} \right] V_{IN}.$$

Usually, the resistance changes are small and the resistances are designed to be almost equal (=R). In that case, $$\Delta V_{OUT} \approx \left[ \frac{\Delta R_A - \Delta R_B + \Delta R_C - \Delta R_D}{R} \right] V_{IN}.$$

The changes in the resistances can be measured directly. They can be also tuned to zero by application of the local gate voltages. Therefore, the signal in sensor D (as shown in FIG. 5) can be given as $$\Delta R_D \approx -R \frac{\Delta V_{OUT}}{V_{IN}}.$$

By measuring the change in the output voltage across the bridge, one can measure the signal change in the sensor D (functionalized sensor). The signal is independent of the resistances A, B and C and the changes in those resistances.

In some embodiments, the nanosensor comprises a nanoscale silicon-based FET device. Many such devices show sensitivity, reliability, robustness and the sensor flexibility needed for many multiplexed diagnostics microarrays. In some cases, the nanoscale devices can be developed and/or implemented on traditional top-down silicon. In some case, by developing and implementing the nanoscale devices on traditional top-down silicon, the reliability and robust quality of top-down silicon semiconductor manufacturing processes can be improved and error rates in testing, both in point-of-care and central reference labs can be reduced. This can result in increased effectiveness of each patient visit to a lab or clinic, reduced cost of diagnosis, and earlier diagnosis, treatment, and monitoring.

U.S. Provisional Patent Application Ser. No. 61/888,830, filed Oct. 9, 2013, and entitled "Differential Sensor Measurement Methods and Structures," is incorporated herein by reference in its entirety for all purposes.

The following examples are intended to illustrate certain embodiments of the present invention, but do not exemplify the full scope of the invention.

Example 1

Figure 7:
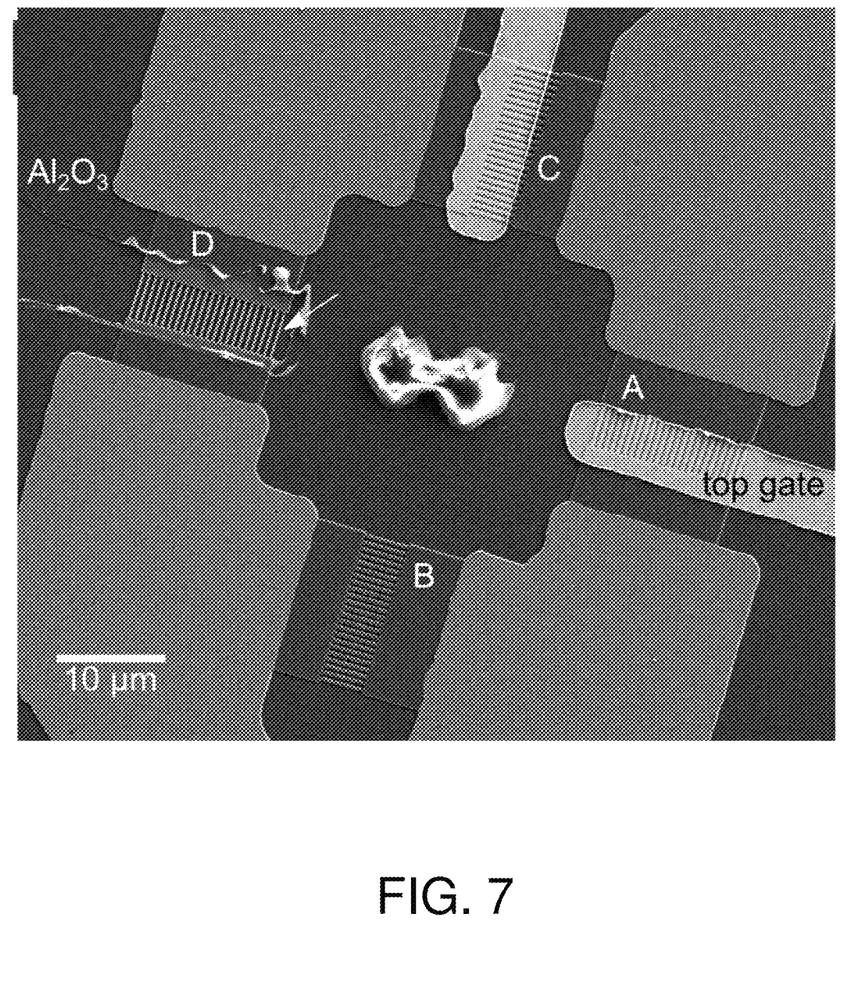
FIG. 7 is a schematic illustration of an exemplary embodiment of an on-chip Wheatstone bridge measurement setup.

This example describes the fabrication of an exemplary system in which multiple nanosensors are arranged in a circuit. Silicon-on-insulator wafers were used as substrates. The sensor system was produced as follows. First, four sets of wires are defined by electron-beam lithography. Typically a set of wires consisted of about 20 wires 10 microns long and 100 nm wide for increased sensitivity. Two different PMMA films (950 and 495) were spun on the wafer as electron-sensitive layers and after exposure the wafer was developed in MIBK. Subsequently, chromium was deposited by evaporation as a mask for subsequent etching. The source and drain electrodes for all four sets of wires were defined by photolithography. After exposure and developing a small titanium layer for improved adhesion, a gold layer was deposited (via evaporation) as the electrode metal. Next, chromium was deposited (via evaporation) as a mask for etching. Reactive Ion Etching was used to etch the unwanted silicon, and afterwards, the chromium was chemically etched. In order to insulate two sets of wires from the gate electrodes previously deposited, PMMA was overexposed on an area covering the wires by electron beam lithography. Afterwards the gate electrodes were defined by photolithography and deposited by titanium and gold evaporation. For the use of the device in solution, the electrodes were covered by an electrically insulating layer. For this purpose, a polymer mask was spun onto the device and using photolithography exposure and developing only the area of one set of wires (without the top electrode) remained covered. Afterwards an 80 nm layer of aluminum oxide was deposited by atomic layer deposition (ALD). Subsequent dissolving of the polymer mask and another deposition of aluminum oxide by ALD (10 nm) also covered the last set of wires and left the device ready for functionalization. One version of a finished device is shown in FIG. 7. In FIG. 7, the top electrodes above wires A and C electrodes can correspond to top gate electrodes and can be used to adjust the resistance of the wires to allow for balanced bridge operation.

Example 2

This example describes the measurement of pH using a nanosensor Wheatstone bridge network and the improvement in the signal-to-noise ratio of such measurements using a nanosensor Wheatstone bridge network as compared to a conventional single nanosensor system.

The nanosensor Wheatstone bridge network was formed as described in Example 1, except a layer of $Al_2O_3$ (60 nm) was deposited by ALD everywhere except on the sensing wires and another thin layer of $Al_2O_3$ (20 nm) was deposited by ALD to cover the whole sample including the wires. The final device consist of two sets of nanowires exposed to fluid, one covered by 20 nm $Al_2O_3$, the other covered by 140 nm $Al_2O_3$, which made the latter less susceptible to changes in the fluid and allowed the detection of different pH values. The other two sets of wires exhibit a tunable resistance by applying appropriate top gate voltages in order to balance the bridge. The nanowire Wheatstone bridges were tested using 2 mM PBS buffer solutions with either NaOH or HCl added to achieve different pH values from 3 to 11. The devices were mounted in a fluid chamber with one inlet and one outlet and a reference electrode, which was grounded throughout the experiment. For constant fluid flow of about 25 l/min a syringe pump (WPI, Sp210iw) was used. Electrical measurements were performed using an EG&G 7260 lock-in-amplifier. An AC voltage at low frequency (37 Hz) was applied to the Wheatstone bridge and the diagonal voltage was measured at the same frequency. A back gate voltage was applied to increase the sensitivity of the wires.

The sensing capability of the nanowires compared to a conventional single nanosensor method was tested. A conventional detection method was simulated by measuring the conductance across wires D shown in FIG. 7 while consecutively pumping buffer solutions exhibiting different pH through the fluid chamber over the device. For the Wheatstone bridge measurements, the device was connected to a lock-in-amplifier and the top gate voltages above two of the sets of wires (e.g., wires A and wires C in FIG. 7) were adjusted to either null the output voltage, hence balancing the bridge, or increasing the output voltage and "pushing" the device further out of balance. The input voltage was kept constant in those cases, as were all other relevant parameters. The balanced bridge had a signal to noise ratio that was five times higher than the bridge "pushed" out of balance and three times higher than the conventional system. Additionally, the overall drift of the balanced bridge signal was significantly reduced.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A structure comprising:
   a first semiconductor nanosensor functionalized with a detector species, the first semiconductor nanosensor comprising a first input pad electrically connected to a first end of the first semiconductor nanosensor and a first detection pad electrically connected to a second end of the first semiconductor nanosensor opposite the first end;
   a second semiconductor nanosensor functionalized with a detector species and in electrical communication with the first semiconductor nanosensor, the second semiconductor sensor comprising a second input pad electrically connected to a first end of the second semiconductor nanosensor and a second detection pad electrically connected to a second end of the second semiconductor nanosensor opposite the first end; and
   a phase shifter electrically coupled with the first input pad of the first semiconductor nanosensor, the second input pad of the second semiconductor nanosensor, and a voltage source, wherein the phase shifter is configured to produce a first signal that is applied to the first input pad and a second signal having a phase that is shifted in phase by 180° relative to the first signal that is applied to the second input pad;
   wherein the first semiconductor nanosensor and the second semiconductor nanosensor are configured to output a differential electrical property between the first semiconductor nanosensor and the second semiconductor nanosensor when exposed to a sample comprising an analyte,
   wherein the first and second semiconductor nanosensors comprise one or more nanowires that are functionalized with the detector species and the nanowires have a cross-sectional dimension of less than or equal to about 150 nm; and
   wherein the nanowires of the first and the second semiconductor nanosensor include an aluminum oxide coating and a thickness of the aluminum oxide coating on the nanowires of the first semiconductor nanosensor is greater than a thickness of the aluminum oxide coating on the nanowires of the second semiconductor nanosensor.

2. The structure of claim 1, wherein the first and second semiconductor nanosensors are positioned on a same chip such that the smallest distance between the first and second semiconductor nanosensors is less than or equal to about 1 mm.

3. The structure of claim 1, comprising a gate associated with the second semiconductor nanosensor.

4. The structure of claim 3, wherein the gate is configured to modulate a signal from the first and/or second semiconductor nanosensor.

5. The structure of claim 3, wherein the gate is positioned over the second semiconductor nanosensor.

6. The structure of claim 3, wherein the gate is positioned to a side of the second semiconductor nanosensor.

7. The structure of claim 3, wherein the gate is configured to receive a voltage and alter at least one electrical property of the second semiconductor nanosensor.

8. The structure of claim 1, wherein the differential electrical property is a differential voltage.

9. The structure of claim 1, wherein the differential electrical property is a differential current.

10. The structure of claim 1, wherein the differential electrical property is a differential conductance.

11. The structure of claim 1, wherein the differential electrical property is a differential resistance.

12. The structure of claim 1, comprising:
    a third semiconductor nanosensor in electrical communication with the first and second semiconductor nanosensors; and
    a fourth semiconductor nanosensor in electrical communication with the first, second, and third semiconductor nanosensors.

13. The structure of claim 1, wherein at least one of the first and second semiconductor nanosensors comprises a field effect transistor.

14. The structure of claim 1, wherein at least one of the first and second semiconductor nanosensors comprises silicon.

15. The structure of claim 1, wherein the first detection pad and the second detection pad comprise a same detection pad used to detect a difference between a first voltage from the first semiconductor nanosensor and a second voltage from the second semiconductor nanosensor.

* * * * *